United States Patent [19]
Meddings

[11] Patent Number: 6,037,330
[45] Date of Patent: Mar. 14, 2000

[54] COMPOSITION FOR SITE SPECIFIC DETECTION OF GASTROINTESTINAL DAMAGE AND METHOD USING THE SAME

[76] Inventor: Jonathan B. Meddings, 16 Varshaven Place NW., Calgary, Canada, AB T3A OE1

[21] Appl. No.: 08/926,966

[22] Filed: Sep. 10, 1997

Related U.S. Application Data

[60] Provisional application No. 60/025,898, Sep. 13, 1996.

[51] Int. Cl.[7] ............................. A01N 43/04; A61K 31/70
[52] U.S. Cl. ................................. 514/53; 436/64; 436/94; 436/811; 436/813
[58] Field of Search ............................... 436/64, 94, 811, 436/813; 514/53

[56] References Cited

U.S. PATENT DOCUMENTS

| | | | |
|---|---|---|---|
| 5,023,072 | 6/1991 | Cheng | 424/9 |
| 5,605,840 | 2/1997 | Meddings et al. | 436/94 |
| 5,620,899 | 4/1997 | Meddings et al. | 436/63 |

FOREIGN PATENT DOCUMENTS

92/00402  1/1992  WIPO .

OTHER PUBLICATIONS

Cobden, I., et al., "Intestinal Permeability And Screening Tests For Coeliac Disease", *Gut,* 512–518 (1980).

Meddings, J.B., et al., "Sucrose Permeability: A Novel Means of Detecting Gastroduodenal Damage Noninvasively", Amer. J. Ther., 2 (11), 843–849 (1995).

Meddings, J.B. et al., "Sucrose: A Novel Permeability Marker For Gastroduodenal Disease", Gastroenterology, 104, 1619–26 (1993).

Sutherland, L., et al., "A Simple, Non–invasive Marker of Gastric Damage: Sucrose Permeability", The Lancet, 343, 998–1000 (1994).

Meddings, J., et al., "Noninvasive Detection of Nonsteroidal Anti–inflammatory Drug–Induced Gastropathy In Dogs"Am. J. Vet. Res., 56, 8, 997–981 (1995).

Menzies, I., "Absorption of Intact Oligosaccharide In Health And Disease", Biochemical Society Transactions 550th Meeting, Englefield Green, vol. 2, 1042–1047 (1974).

*Primary Examiner*—James O. Wilson
*Assistant Examiner*—Howard Owens
*Attorney, Agent, or Firm*—Fitzpatrick, Cella, Harper & Scinto

[57] ABSTRACT

Disclosed is a composition for the site-specific detection of gastrointestinal damage containing (a) a first disaccharide that does not degrade in the colon, small intestine or stomach; (b) a second disaccharide that degrades in the colon but does not degrade in the small intestine or stomach; and (c) a third disaccharide that degrades to its monosaccharides in the small intestine and not in the stomach. A method for the site-specific detection of gastrointestinal damage employing the composition of the invention is also disclosed.

13 Claims, 8 Drawing Sheets

COMPOSITION FOR SITE SPECIFIC DETECTION OF GASTROINTESTINAL DAMAGE AND METHOD USING THE SAME

This invention claims the benefit of U.S. Provisional Application No. 60/025,898, filed Sep. 13, 1996.

BACKGROUND OF THE INVENTION

1. Field of the Invention

This invention relate to a composition of disaccharides that is useful for the non-invasive site-specific detection of gastrointestinal damage.

2. Related Background Art

Damage to the gastrointestinal tract can present a serious health risk. Therefore it is important to be able to locate the site of such damage within the gastrointestinal tract, i.e., the stomach, small intestine or colon, so that an appropriate treatment can be prescribed.

Stomach ulcers are one form of gastrointestinal damage which can pose a serious health threat as in many instances ulcers are asymptomatic. Since stomach ulcers can develop and be present without any symptoms the damage caused by the ulcers to the stomach and the bleeding associated with such ulcers presents a serious health risk which can be fatal. In the past, damage to the gastric epithelial cells was detected using endoscopies of the patients, x-ray examinations after ingesting a barium meal or through the introduction of a radio-labeled compound having an affinity for damaged epithelial cells. These treatments, however, are invasive or require the use of radioisotopes or x-rays.

PCT International Application No. WO92/00402 describes a non-invasive method for detecting gastric epithelial damage using a disaccharide such as sucrose, maltose or lactose which is orally administered to a patient followed by assaying the patient's blood or urine for the disaccharide to determine the existence and extent of gastric epithelial damage. While this advantageous method overcomes the problems associated with invasive or radioisotopic methods, it does not reliably detect damage of the intestinal tract.

Disorders to the small intestine and the colon also present significant health risks. Such disorders include, for example, carcinoma, benign lesions, Crohn's disease, colitis and the like. Cobden, I., et al., "Intestinal permeability and screening tests for coeliac disease", *Gut,* 21, 512–518 (1980) describes an assay for ascertaining damage to the small intestine using a combination of cellobiose and mannitol. However, this assay does not provide information on damage to the stomach or colon.

Meddings, J. B., et al., "Sucrose Permeability: A Novel Means Of Detecting Gastroduodenal Damage Noninvasively", Amer. J. Ther., 2(11), 843–849 (1995), disclose the use of a mixture of sucrose, lactulose and mannitol to show that increased sucrose permeability is a measure of damage to the stomach and not the small intestine. However, such a mixture does not provide a means of assaying the colon.

It would be desirable to provide a composition and method using such a composition for detecting site-specific gastrointestinal damage, i.e., the stomach, small intestine or colon, that is non-invasive and non-radioisotopic to alleviate both patient discomfort and the use, handling and disposal of radioactive isotopes. It would also be highly desirable to have such a site-specific gastrointestinal damage detection composition that could be readily used by practitioners in a simple setting (such as an office) to identify any damage to the gastrointestinal tract. Such a procedure would be helpful in the early diagnosis and thereby early treatment of a potentially serious condition.

SUMMARY OF THE INVENTION

This invention is directed to a composition for site-specific detection of gastrointestinal damage. The composition comprises (a) a first disaccharide that does not degrade in the colon, small intestine or stomach; (b) a second disaccharide that degrades in the colon but does not in the small intestine or stomach; and (c) a third disaccharide that is degraded to its monosaccharides in the small intestine and not in the stomach. Preferably, the first disaccharide is sucralose, the second disaccharide is lactulose and the third disaccharide is sucrose. The composition also preferably contains mannitol.

Another embodiment of the invention is directed to a composition for detecting damage to the intestines comprising (a) a first disaccharide that does not degrade in the colon, small intestine or stomach; (b) a second disaccharide that degrades in the colon but does not degrade in the small intestine or stomach. The preferred first and second disaccharide are sucralose and lactulose, respectively.

The invention is also directed to a method for site-specific detection of gastrointestinal damage employing the composition of this invention containing (a), (b) and (c). The invention is also related to an improved method for detecting damage to the intestines with a composition comprised of (a) and (b).

The compositions of this invention are orally administered to the patient and then the patient's urine is assayed for the presence of the disaccharides which were orally administered. A value determined in the assay which is greater than a normal control value for the disaccharide in the urine is indicative of gastrointestinal damage. The particular disaccharide(s) detected is used to ascertain the specific site of the damage. In addition the assay value for each disaccharide can be correlated with control values to determine the magnitude of the gastrointestinal damage at each affected site.

BRIEF DESCRIPTION OF THE DRAWINGS

The invention herein will be better understood with regard to the following detailed description and the accompanying drawings wherein:

FIG. 8(*b*) is a graph showing sucrose/lactulose ratio and sucrose excretion compared to the dosing agent.

DETAILED DESCRIPTION OF THE INVENTION

Figure 1:
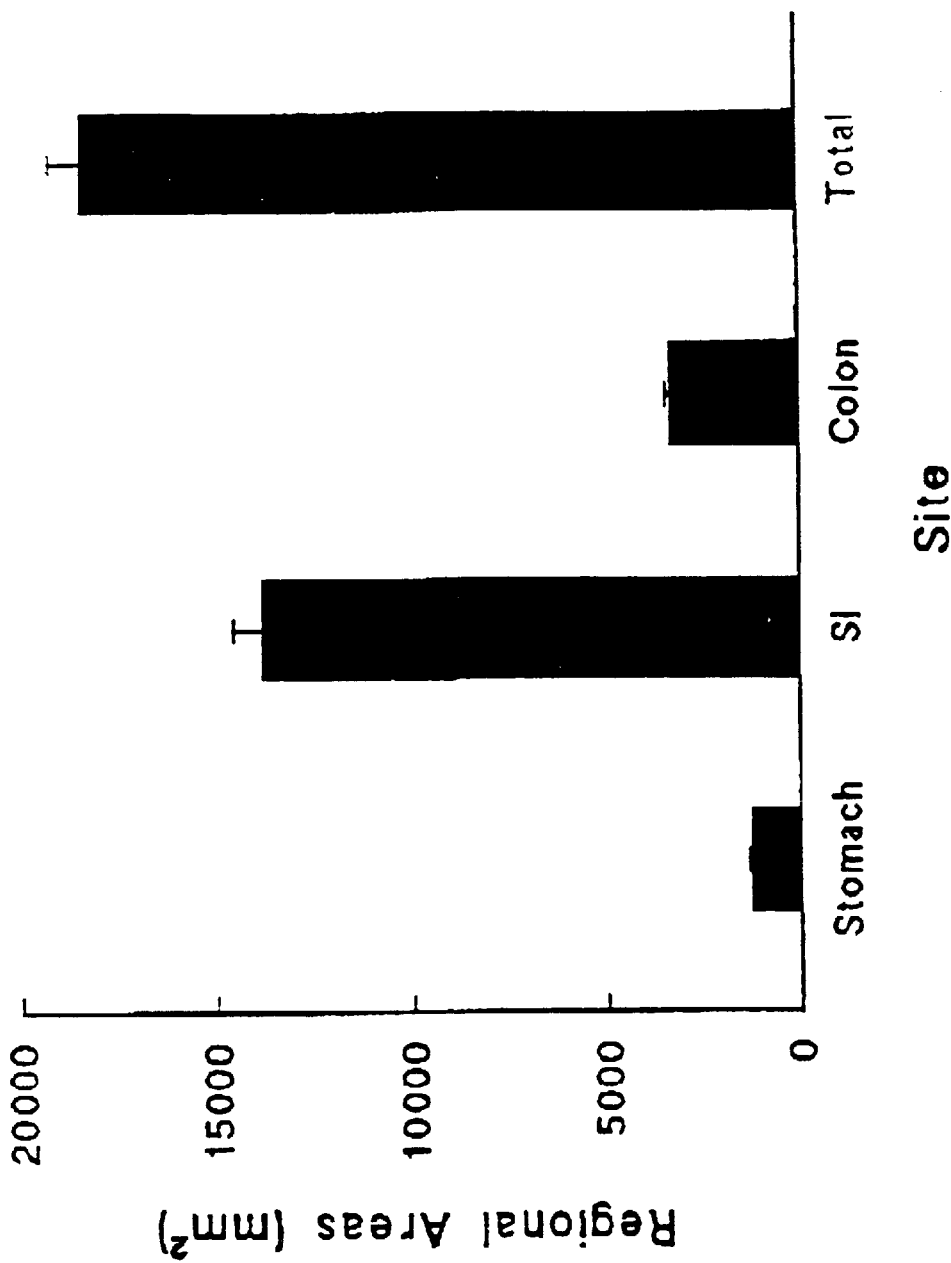
FIG. 1 is a graphic illustration of the various gastrointestinal segments of the rat and the relative surface area of each.

In one embodiment of the invention the composition is useful for the site-specific detection of gastrointestinal damage and comprises (a) a first disaccharide that does not degrade or metabolize in the colon, small intestine or stomach, (b) a second disaccharide that degrades in the colon but does not degrade or metabolize in the small intestine or stomach, and (c) a third disaccharide that degrades or metabolizes in the small intestine and not in the stomach. As used herein, the term degrades includes any mechanism which converts the disaccharide to any of its components such as by metabolic, enzymatic or bacterial degradation pathways.

Yet another embodiment of the invention is a composition comprising (a) the first disaccharide and (b) the second disaccharide. This composition provides a particularly sensitive assay composition for detecting small intestinal damage.

The compositions of this invention may be, for example, in the form of a solid (e.g., tablet), powder or liquid, such as a solution, suspension or emulsion.

The disaccharides employed in the composition of this invention are water soluble and are not substantially transported across cell membranes (microgram quantities may be found in urine). The disaccharides are not substantially broken down elsewhere in the body which enables their detection in the urine of a patient in the event of gastrointestinal damage.

The first disaccharide is particularly characterized by its lack of degradation in the gastrointestinal tract, i.e., the stomach, small intestine and colon. As expressed herein, degradation includes more than insubstantial breakdown of the disaccharides by metabolic, bacterial or any other pathway. A particularly preferred first disaccharide is sucralose. Other halogenated or likewise modified disaccharides that are resistant to bacterial degradation or digestion can be used. Generally, the first disaccharide is present in an amount between about 1 to about 3 percent by dry weight of the total composition. As expressed herein, the "weight of the total composition" is the combined weight of the first disaccharide, second disaccharide and third disaccharide along with any mannitol present.

The second disaccharide is particularly characterized by its degradation in the colon, but not in the small intestine or stomach. Preferred second disaccharides include lactulose and cellobiose. Lactulose is most preferred. Generally, the second disaccharide is present in an amount between about 4 to about 10 percent by dry weight of the total composition.

The third disaccharide is particularly characterized by its degradation in the small intestine to its monosaccharides, but not in the stomach. Preferred third disaccharides include sucrose, maltose and lactose. The most preferred third disaccharide is sucrose. Generally, the third disaccharide is present in an amount between about 87 to about 95 percent by dry weight of the total composition.

The composition of this invention also preferably contains mannitol. When present, mannitol is typically included in an amount between about 1 to about 3 percent by dry weight of the total composition.

A particularly preferred composition of this invention contains sucralose in an amount of about 1.5 to about 2.5 percent by dry weight of the composition, lactulose in an amount of about 4 to about 6 percent by dry weight of the composition, sucrose in an amount of about 91 to about 92 percent by dry weight of the composition and mannitol in an amount of about 1.5 to about 2.5 percent by dry weight of the composition. A composition containing about 2 grams sucralose, about 5 grams lactulose, about 100 grams sucrose and about 2 grams mannitol made up in water to about 450 ml is a preferred composition for administration to a patient.

As noted previously, another embodiment of the invention includes a composition containing the first and second disaccharides, but not the third disaccharide. In this case, the first disaccharide is generally present in an amount between about 10 to about 75 percent dry weight of the disaccharides, while the second disaccharide is generally present in an amount between about 25 to about 90 percent dry weight of the disaccharides.

The properties of the above-described disaccharides allow the composition containing the disaccharides (a), (b) and (c) to be employed as assay compositions for the site-specific detection of gastrointestinal damage. For example, if there is gastrointestinal damage at any one of the stomach, small intestine or colon, the first disaccharide is capable of passing through the damaged cells into the blood stream of the patient. Permeation is proportional to the total gastrointestinal damage.

On the other hand since the second disaccharide degardes in the colon, it will only permeate across damage in the stomach and small intestine. Therefore, a combination of the first disaccharide and the second disaccharide may be employed to assay damage to the colon and rule out damage to the small intestine. Since the third disaccharide metabolizes in the small intestine, it will be substantially limited to permeation of damaged epithelial cells in the stomach. Therefore, the combination of the third disaccharide with the first and second disaccharide provides an advantageous non-invasive means to determine whether damage is present in the stomach, the small intestine, the colon or any combination thereof.

The inclusion of mannitol in the composition of this invention containing lactulose allows for the calculation of the ratio of lactulose to mannitol in the urine, which is a known indicator for small intestine damage. It has now been found that a more sensitive indicator of small intestine damage is provided by a composition containing both lactulose and sucralose which provides for the assay of the lactulose/sucralose ratio in the urine.

The extent of the disaccharides found in the urine provides a means of determining not only the site of the damage but the extent of that damage. That is the greater the extent of the damage to a particular site in the gastrointestinal tract the greater the permeability of the available disaccharides at that point in the gastrointestinal tract.

This invention may be practiced by orally administering the site-specific gastrointestinal assay composition to a patient. In a particularly preferred practice of the method of this invention, the patient can fast for a sufficient amount of time, such as six to twelve hours or six to eight hours, prior to ingesting or administering the composition of this invention. The method is practiced by administering a known amount of composition containing a known amount of disaccharides. It is desirable to administer an amount of the composition containing a sufficient amount of the disaccharides to facilitate the subsequent recovery and assay of those disaccharides. However, the amount of disaccharides administered to the patient need only be that amount which is effective to show a presence in the urine as a result of damage to the gastrointestinal tract. Such amounts can be readily determined by those skilled in the art without undue experimentation.

Following the administration of the composition of this invention, the patient's total urine output can be collected over a period of time. The total urine output could be collected for up to twenty-four hours. The urinary collection can be from the first evacuation of the patient up to 24 hours thereafter. It is believed that the total urine output of a patient 24 hours after administration of the composition of this invention is an effective and sufficient amount of time for detecting the disaccharides in the urine.

The collected urine is then assayed for the presence of the disaccharides in the administered composition. Any suitable assay technique can be followed. That is any standard or customary assay procedure for the appropriate disaccharides in the urine can be used. It is preferable that the assay be a quantitative assay so that the amounts of disaccharides determined from the assay can be correlated to the extent of gastrointestinal epithelial damage. In this regard, an empirically derived scoring system can be derived using healthy volunteers and individuals with lesions. On the other hand, a qualitative assay can be useful for specifying the site of damage in the gastrointestinal tract.

With damage to the epithelium in the gastrointestinal tract, there is a greater permeation of disaccharides across the point(s) of damage. The disaccharides employed in the composition of this invention, particularly the combination of sucralose, lactulose and sucrose provide unique markers to ascertain the site of epithelial damage in the gastrointestinal tract in a safe and non-invasive manner.

Experimental Rat Models
Acetylsalicylic Acid (ASA) Dosing 100 ml of 1.3% Carboxymethylcellulose (CMC) was made. Appropriate amounts of CMC were dissolved in $H_2O$, stirred for one hour and then sonicated for 1 hr. Acetylsalicylic acid was suspended in these solutions at a final concentration of either 100 or 250 mg/ml.

Both suspensions were sonicated for 2 hrs. prior to dosing of rats and were shaken immediately prior to dosing. The temperature of the suspension rose during sonication to make the suspension more fluid.
Dosage protocol Male wistar rats were fasted overnight while housed three rats per cage. Cages were fitted with stainless steel fasting racks to prevent the rats from eating their own feces. Water was taken away from rats two hours prior to dosing with ASA.

Rats were numbered and weighed immediately prior to dosing. The weights of rats and volumes of suspensions given were recorded for later reference.

Rats were given ASA suspensions based on 100 mg/kg or a 250 mg/kg dosage schedule in a single dose. Solution was given via stainless steel feeding needle (18 gauge, 6 cm long with a 2.25 mm diameter round tip) attached to a 1 to 5 ml syringe.

Next, rats were placed back in their cages for two hours until they were either given a site-specific gastrointestinal assay composition of this invention or sacrificed for damage scores.
Indomethacin Dosing All Indomethacin solutions were made in a 5% $Na_2CO_3$ solution. For a 10 mg/kg Indomethacin dosage 100 mg. of Indomethacin was dissolved in 10 ml of 5% $Na_2CO_3$ solution. This made a 10 mg/mL solution. For a 5 mg/kg Indomethacin dosage 50 mg of Indomethacin was dissolved in 10 ml of 5% $Na_2CO_3$ solution. This made a 5 mg/mL solution. The solutions had to be heated to allow Indomethacin to dissolve. This was done by covering the flask containing the solution with a stopper, wrapping it in parafilm and then running under hot tap water for 10 min.
Dosage protocol Rats were numbered and weighed immediately prior to dosing. The weights of rats and values of solutions given were recorded for later reference.

Rats were given Indomethacin solution based on 10 mg/kg or 5 mg/kg in a single dose. The solution was given via stainless steel feeding needle (18 gauge, 67 cm long with a 2.25 mm diameter round tip) [Fine Scientific Tools] attached to a ml syringe.

The rats were allowed water but no food for the next 22 hours. Male wistar rats were housed three rats per cage. The cages were fitted with stainless steel fasting racks to prevent the rats from eating their own feces. At the end of the twenty-two hours, rats were given a site-specific gastrointestinal assay composition of this invention or were sacrificed for damage scores.
TNBS (trinitrobenzene sulfonic acid) Dosing A 50% ETOH (v/v) solution was made using double distilled $H_2O$. TNBS was weighed out to make a 20 mg/ml solution in the 50% EtOH solution.
Dosage Protocol Male wistar rats were anesthetized one at a time using methoxyflurane. The rats were placed in a closed container with a small amount of the anesthetic on a gauze pad. Once asleep rats were numbered, weighed and TNBS administered (30 mg or 1.5 ml per rat) via a rectal tube. The tube was made up of soft 18 gauge plastic tygon tubing inserted over an 18 gauge needle that had the point cut off. Care must be taken in inserting the tygon tubing to reduce the risk of perforating the bowel. A needle similar to the 6 cm oral dosing needle described, infra, but which is 8 cm long, can be employed in place of the tygon tubing if desired. The end of the tube was lubricated with water based examination jelly and inserted up to a distance of 8 cm that was marked on the tube with permanent felt marker. The rats were held pointing nose down for 10 seconds and then the anuses of the rats were pinched against the tube and the tube was slowly removed. The rats were then gently placed back into their cages.

Rats were checked every day to ensure that they were alive as TNBS at 30 mg doses has been reported to have a significant mortality rate. The rats were allowed to sit for a period of one week at which time most of the diarrhea that accompanies this method had stopped. This point is important as it is impossible to separate liquid stool from urine during the collection.

Rats where then fasted over night and given a site-specific gastrointestinal assay composition of this invention. After urine was collected the rats were immediately sacrificed using $CO_2$ asphyxiation and the entire gut was opened to check for damage in all areas. Dosage in each area was recorded and presented as a percentage of total gut area.

FIG. 1 illustrates the surface areas of the various gastrointestinal segments of the rat. In all cases measurements were obtained by simply measuring length by width of the visual surface area. As such, these measurements do not reflect the cell density or the microscopic amplification of surface area in the various regions of the gut. Furthermore, the cecal dimensions are not recorded as this segment of the colon was difficult to dissect out in these animals. However, these measurements do provide a rough means of assessing intestinal surface area.

It can be seen from FIG. 1 that the vast majority of gastrointestinal surface area resides within the small intestine. Close to 80 percent of the rat's gastrointestinal surface area is found in this organ. The stomach and colon comprise a much smaller fraction.

Figure 2:
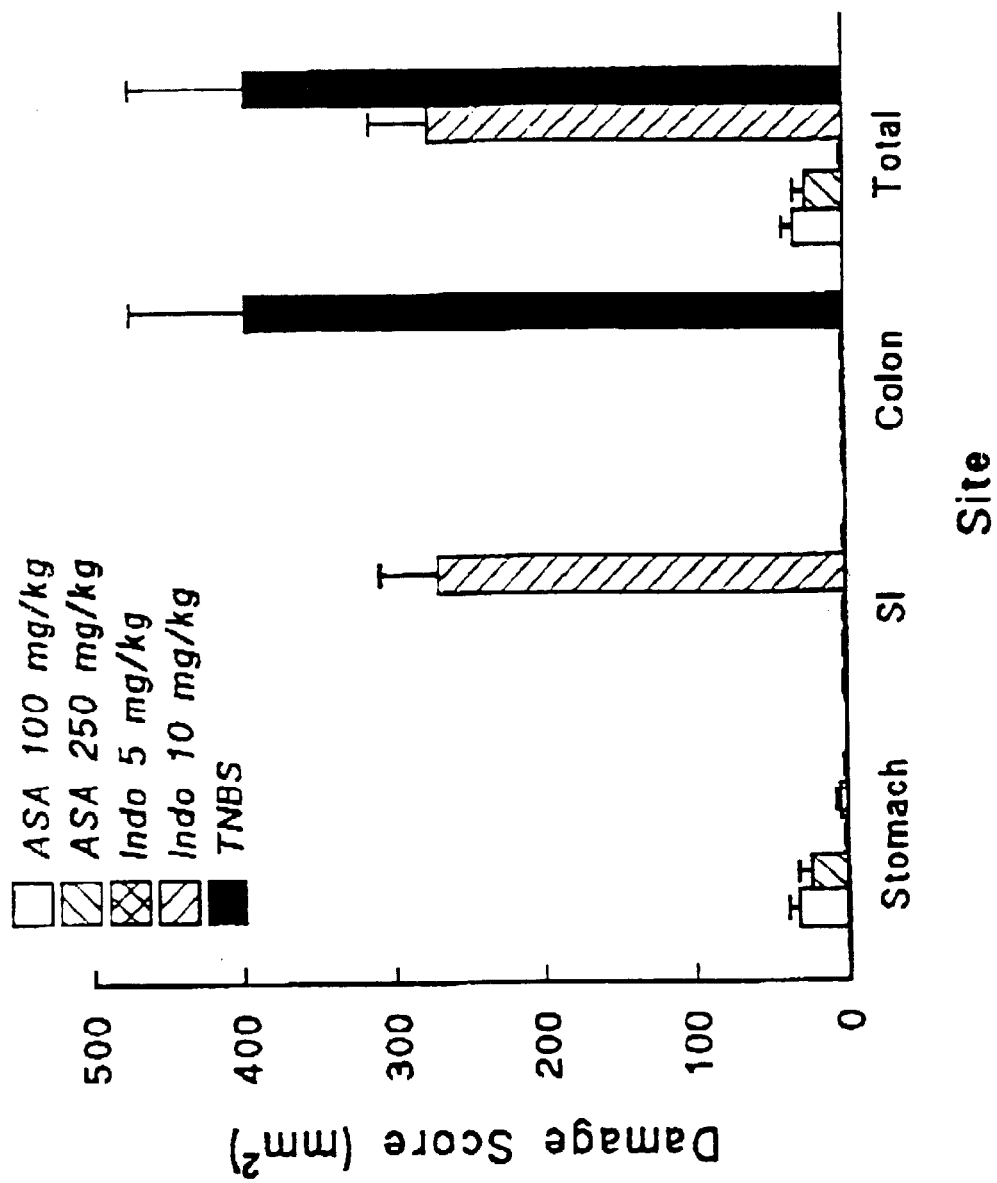
FIG. 2 is a bar graph indicating the amount of damage observed for the stomach, small intestine, colon and total gastrointestinal tract after exposure to various damaging agents at various doses.

FIG. 2 illustrates the amount of damage induced by the various manipulations that were performed in the rat dosing experiments. In this figure damage is separated into either the stomach, small intestine, colon, or the sum of the three preceding organs. Aspirin given in either of the two dosages used prompted damage only to the stomach. In contrast, indomethacin produced both small intestinal and gastric damage at the higher concentration while the lower concentration elicited no visible damage in either organ. It is important to note that neither aspirin nor indomethacin, at any dose, prompted colonic damage. Only treatment with TNBS elicited any significant colonic damage. Therefore, this figure shows that the rat dosing experiments provide specific models for colonic and gastric damage. The indomethacin model appears to produce primarily small intestinal damage with a variable, but lesser, degree of gastric damage.

Figure 3:
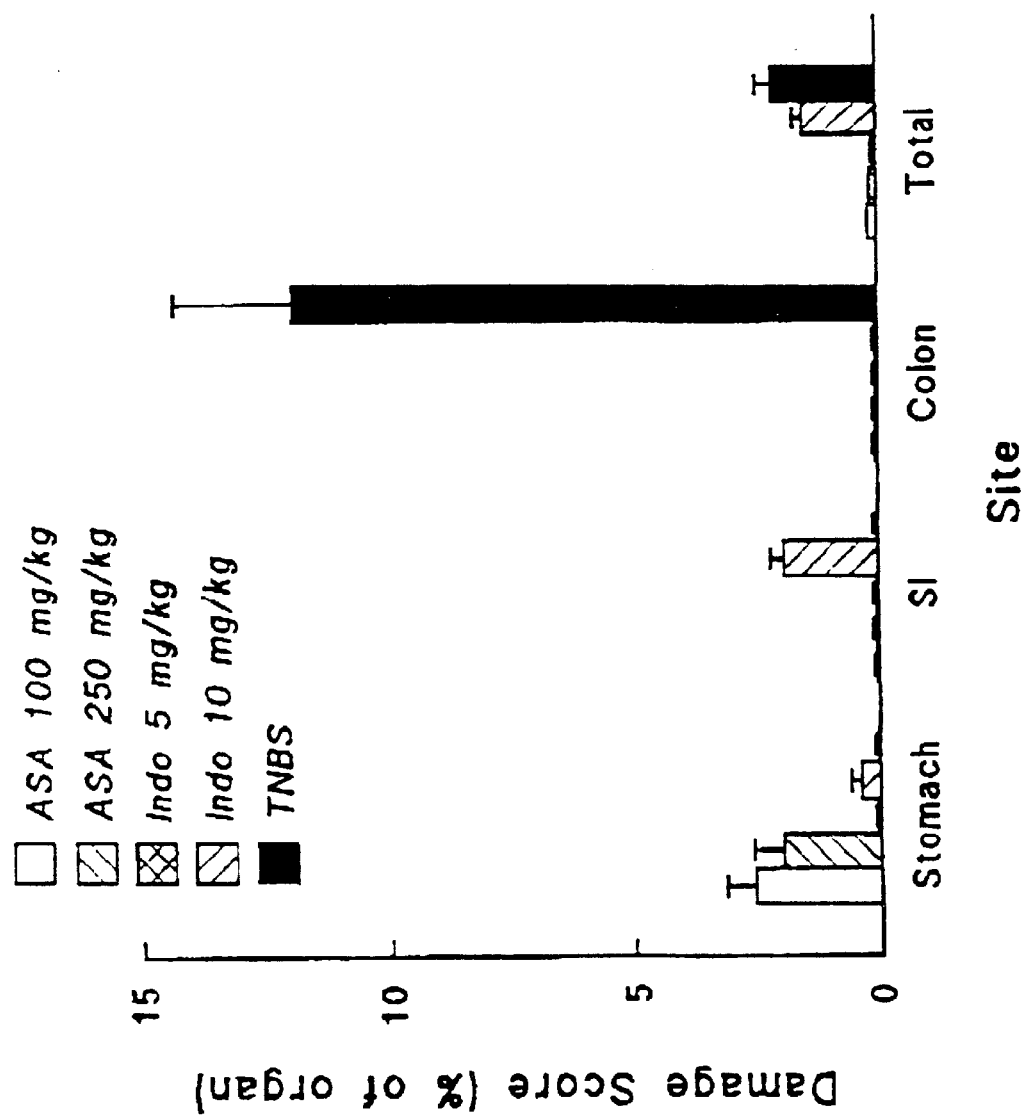
FIG. 3 is a bar graph that illustrates the percent of the organ damaged after exposure to various dosing agents.

Since the total surface area of these three organs varies so much the data is represented as a function of individual organ surface area in FIG. 3. In this figure damage by each modality has been presented as a percentage of total organ surface area. Examination of FIG. 3 clearly illustrates that aspirin significantly damages the stomach alone. Both dosages prompt a 2–3 percent damage rate. In contrast, indomethacin produces significantly lower amounts of gastric damage but a similar proportion of damaged small intestine. Finally, TNBS produces a tremendous amount of colonic damage. Using this agent between 10 and 15 percent of the colonic surface area is involved with macroscopically visible damage. It is important to note that this means of determining damaged surface area can be misleading. In each case only visible damage can be scored. Each of the agents produces different visual patterns of damage. For instance, it is relatively simple to quantify hemorrhagic or ulcerative damage. These are particularly common with either aspirin or TNBS. Indomethacin tends to produce a far more diffuse lesion. Following treatment with this agent the intestine appears thinner and while covered with a clear exudate does not have the degree of hemorrhagic or ulcerative damage seen with the other agents. However, this data can be used as a rough marker for gastrointestinal damage.

The Example which follows is intended as an illustration of a preferred embodiment of the invention, and no limitation of the invention is implied.

EXAMPLE 1

A composition for site-specific detection of gastrointestinal damage was prepared by dissolving 50 g sucrose, 4 g mannitol, 9 ml of "Laxilose" (667 mg/mL Lactulose) [Technilab, Montreal, Quebec, Canada], and 12 ml of "Splenda" (25% w/v sucralose) [McNeil Consumer Products Company, Guelph, Ont., Canada] in double distilled $H_2O$ to a volume of 100.00 ml. Enough composition was made so that each rat could be given 2.0 ml of the composition in one dose. Therefore, each rat received 1 g sucrose, 120 mg lactulose, 80 mg mannitol and 60 mg sucralose in a total volume of 2 ml.

Assay

Male wistar rats (250–300 g), housed three to a cage were fasted overnight prior to administration of the above-described composition. Cages were fitted with stainless steel fasting racks to prevent the rats from eating their own feces. Rats were allowed free access to water up until two hours before dosing. The composition was given via a stainless steel feeding needle (18 gauge, 6 cm long with a 2.25 mm diameter round tip) attached to a 5 mL syringe. All rats were given a 2.0 ml dose. Care was taken to ensure that the probe was inserted down the esophagus and not down the trachea and into the lungs.

The rats were placed into stainless steel metabolic cages with wire bottoms to separate feces from urine. Plastic tubes were mounted underneath a spout on the bottom of each cage to collect urine. As an additional filtering method fine Nylon mesh (300 micron perforations) [Small Parts INC., Florida, USA] was folded into a funnel shape and placed between the spout for each cage and the plastic tubes.

The rats were denied access to water for another three hours at which point they were allowed free access to water for the remainder of the experiment.

Urine was collected for a total of 24 hours at which point the rats were returned to their normal cages. Urine volumes were measured and recorded and the urine composition was analyzed by high performance liquid chromatography (HPLC).

HPLC methods for analyzing sucrose, lactulose and mannitol in urine are well known to those of ordinary skill in the art. See e.g., Meddings, J. B., et al., "Sucrose: a novel permeability marker for gastroduodenal disease", *Gastroenterology*, 104, 1619–26 (1993). Sucralose was also analyzed by HPLC using a Dionex Carbopac MA1 column coupled to a MA1 Guard column. The mobile phase was 500 mM sodium acetate and 0.2% acetic acid (pH=5.5). Following infusion of the sample, a post column alteration was made by the addition of 300 mM NaOH at a flow rate of about 0.2 mL/min. The mobile phase flow rate was about 0.4 mL/min. In this manner the pH of the eluent was increased to over 12 and the sucralose was detected (Detector: ED40 with gold electrode & Ag/AgCl reference electrode) on a gold electrode using pulsed amperometric detection.

Results

Figure 4:
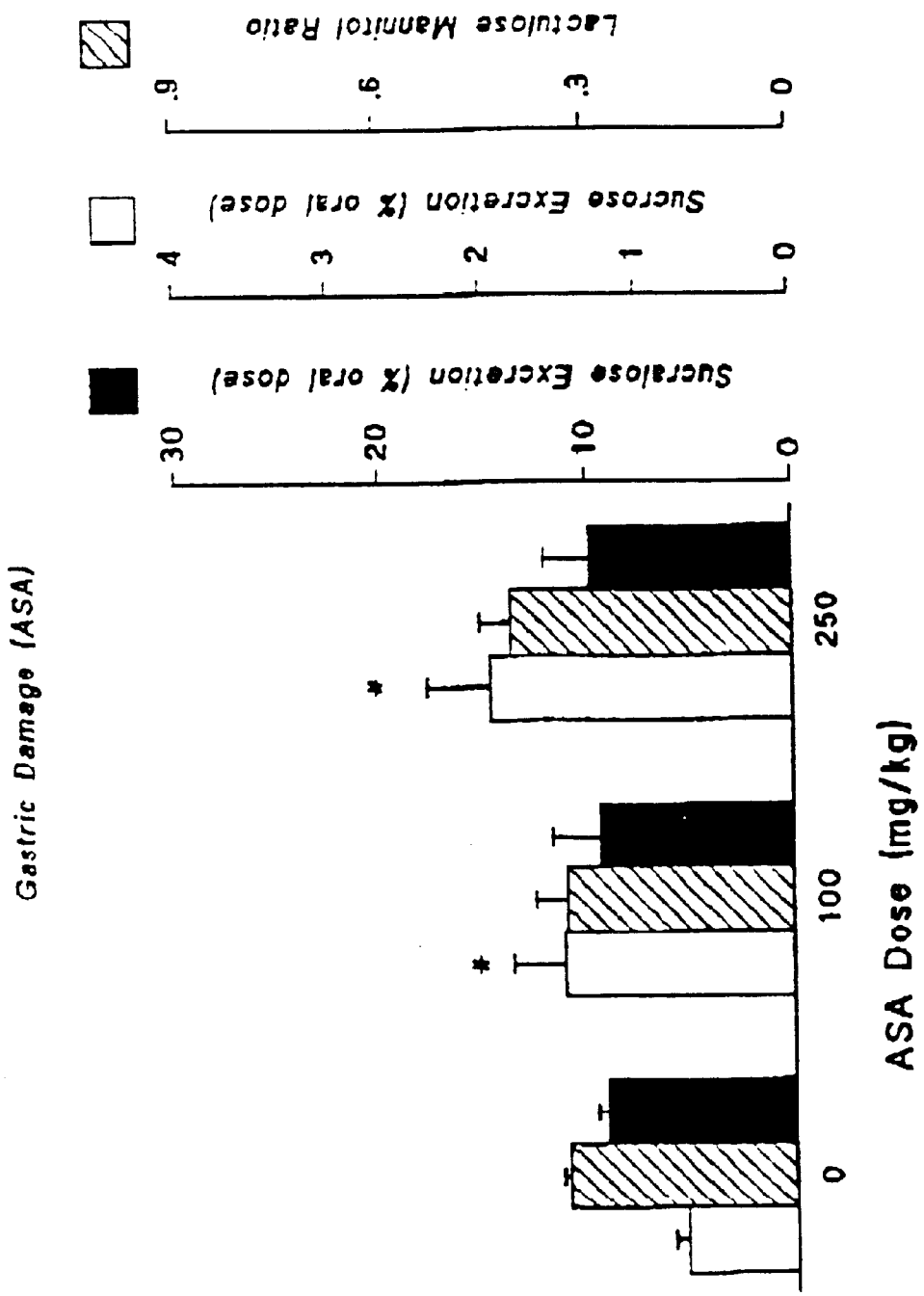
FIG. 4 is a graph illustrating damage to the stomach caused by aspirin dosing.

FIGS. 4 to 8(*b*) present the data for the composition of this invention used in the ASA, Indomethacin and TNBS models of damage. In each case it is important to understand which organ has been damaged. In FIG. 4, only damage to the stomach caused by aspirin is examined. The horizontal axis represents the dose of aspirin given to these animals. Three vertical axes are shown for sucrose, lactulose and mannitol and sucralose. The data has been presented in this fashion as the absolute numbers for each measurement vary greatly.

Considering first the solid bars, it can be seen that sucralose excretion does not increase regardless of the degree of gastric damage. This is in keeping with the relatively small surface area of the stomach. Despite significant damage to the gastric epithelium sucralose excretion does not increase. The same pattern is evident for the lactulose/mannitol ratio. Since this measurement is known to be sensitive to small intestinal damage it is not unexpected that this ratio remains constant. In contrast to these data the rate of sucrose excretion increased dramatically and in proportion to the degree of gastric damage. Therefore, these results show that sucrose excretion is a reliable indicator of gastric damage.

Figure 5:
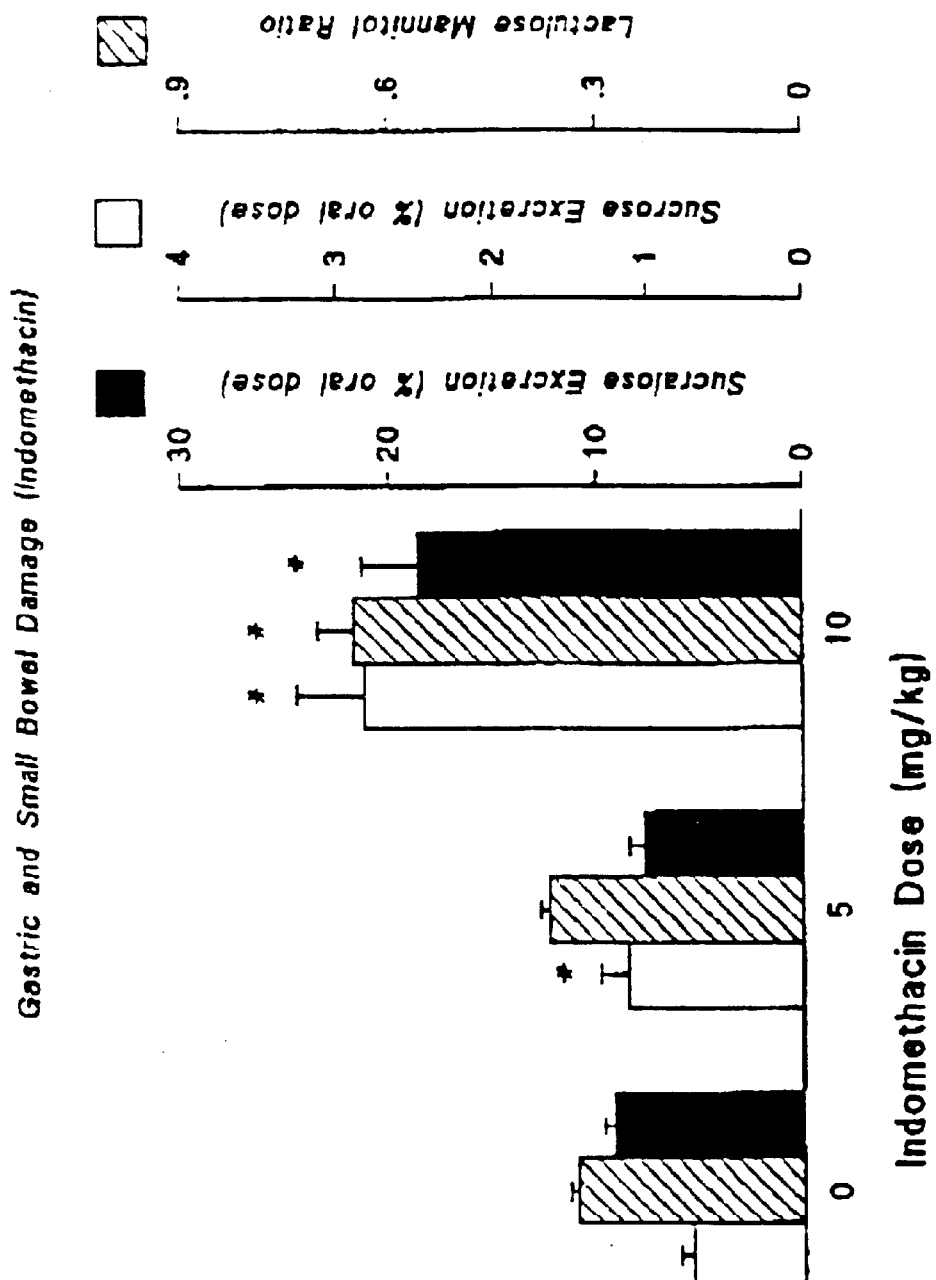
FIG. 5 is a graph illustrating damage to the stomach and small intestine caused by indomethacin dosing.

FIG. 5 illustrates the data obtained after administration of the composition of Example 1 to rats having indomethacin induced gastric and small intestine damage. Gastric damage is clearly evident with the increase in sucrose excretion. Significant increases in the excretion of sucrose occurred at a dose of five mg per kg. In addition, the lactulose/mannitol ratio also increased but only at a higher dose of indomethacin. One interpretation of these data would be that indomethacin prompts gastric damage at a low dose while at higher doses both gastric and small intestinal damage occurred. However, it is believed that the lactulose/mannitol ratio is insensitive to small amounts of small intestinal damage.

Sucralose excretion did not increase with the low dose of indomethacin. However, at the higher concentration significant increases in sucralose excretion were observed. Therefore, sucralose will detect small intestinal damage elicited by indomethacin.

Figure 6:
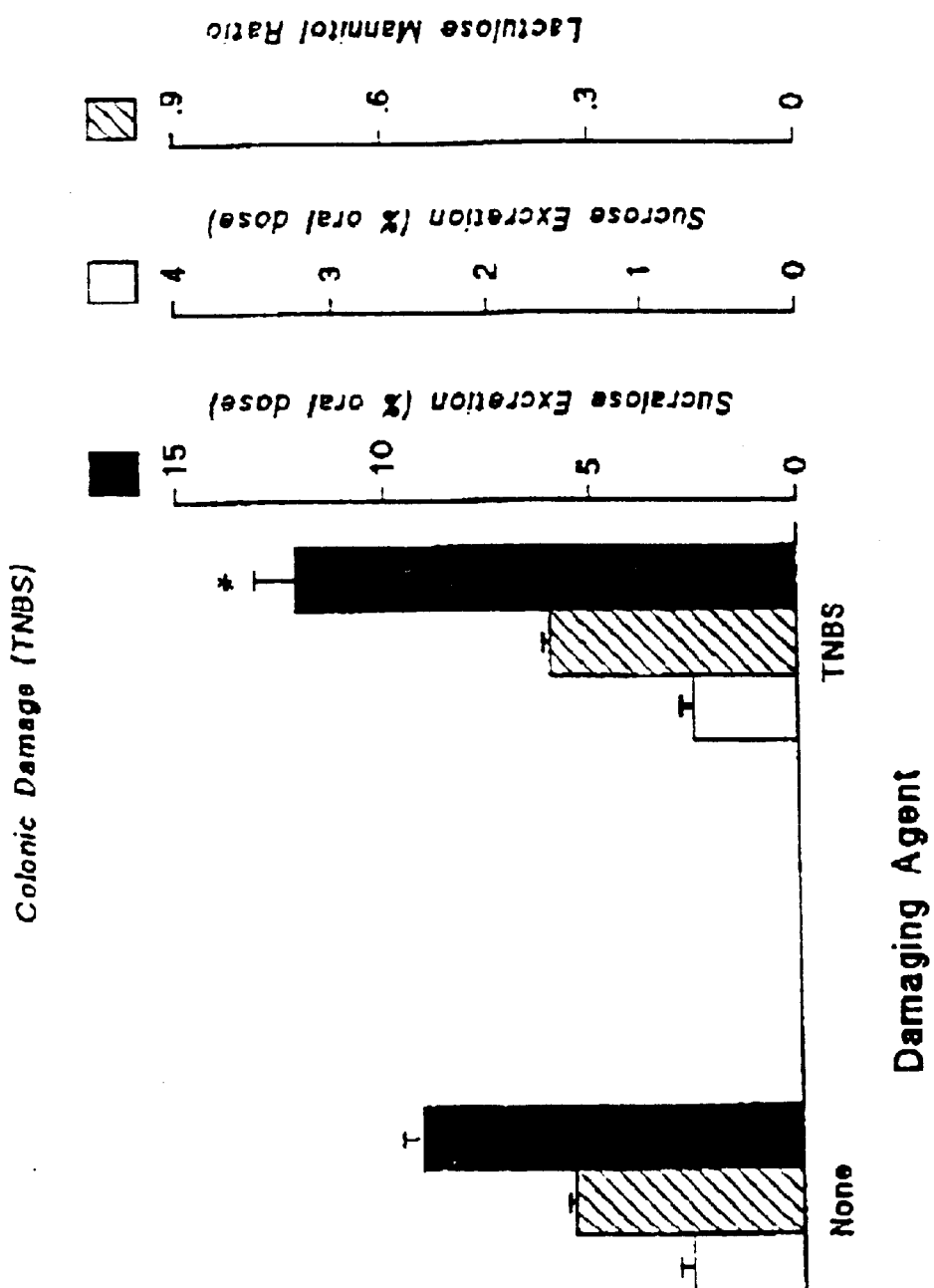
FIG. 6 is a graph illustrating damage to the colon caused by trinitrobenzene sulfonic acid (TNBS).

FIG. 6 illustrates the data obtained by administering the composition of this invention to a rat model having colonic damage induced by TNBS. Under these conditions neither sucrose nor lactulose/mannitol excretion increased. These data confirm the specificity of these disaccharides to more proximal gastrointestinal damage. Sucralose clearly detected the colonic damage produced in this experiment. Although the increase in excretion was relatively small, this comports with the fact that the colonic surface area is also a relatively small fraction of total gastrointestinal surface area.

Figure 7:
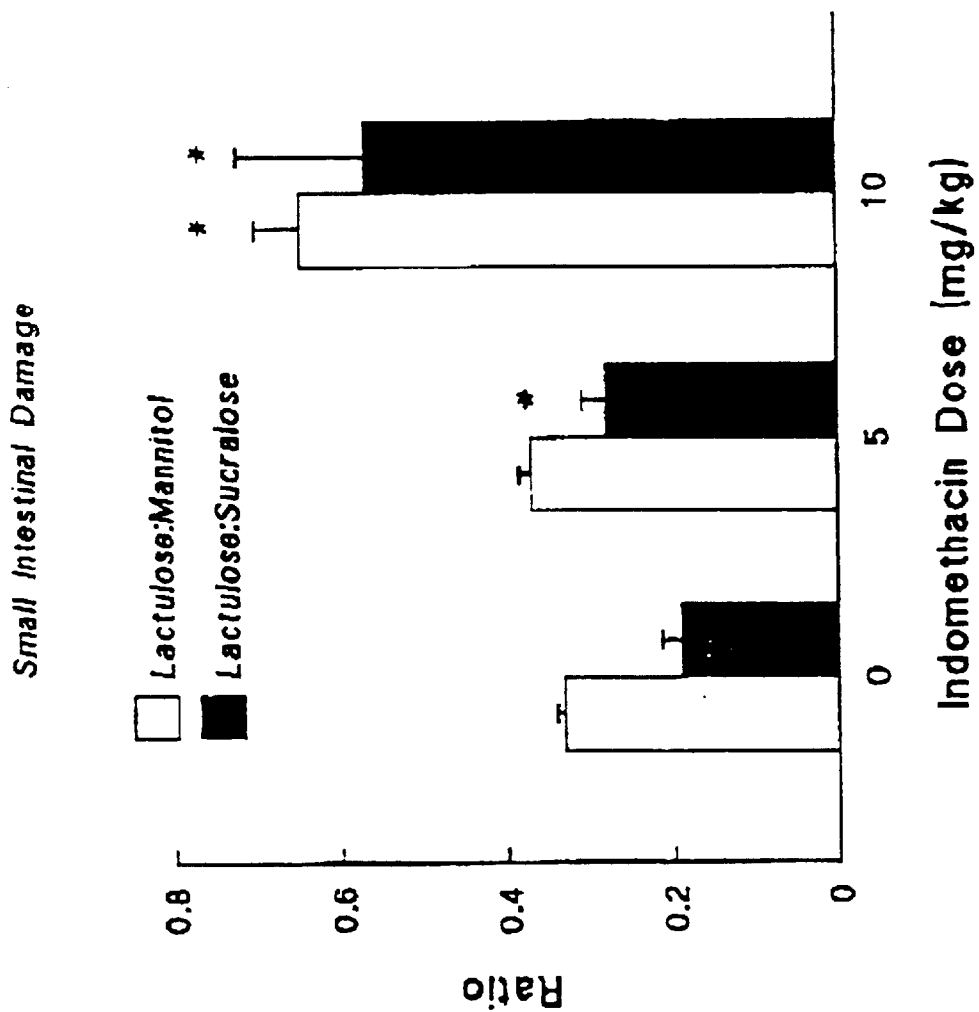
FIG. 7 is a graph illustrating small intestinal damage caused by indomethacin dosing.

FIG. 7 examines the problem of small intestinal damage elicited by indomethacin. Traditionally this type of damage has been quantified with a lactulose/mannitol ratio. The rationale for this has been that mannitol can assess the small intestinal surface area. Since lactulose measures the degree of damage in this organ the ratio reports damage per unit surface area. However, the permeability pathways for lactulose and mannitol are significantly different. Lactulose is a much larger molecule than mannitol and, therefore, traverses the epithelium by a different route than mannitol. Sucralose is of a similar size to lactulose, and presumably penetrates the epithelium by a similar pathway. Since it is not degraded within the gastrointestinal tract it can report the total surface area available for permeation. Therefore, a lactulose sucralose ratio represents a measurement of how permeable the small intestine is as a proportion of total surface area. In control animals (those given no indomethacin) this ratio approximates 0.2. This would imply that the effective small intestinal surface area appreciated by lactulose represents about 20 percent of the total. With significant small intestinal damage at the 10 mg per kg dose of indomethacin this fraction increases to almost 60%. Since the absolute small intestinal surface area did not increase these data are best interpreted as significant small intestinal damage. Under this interpretation, it is illuminating to examine the lower indomethacin dosage. Using the traditional lactulose/mannitol ratio no damage was apparent. However, using this more novel approach the lactulose/sucralose ratio was significantly elevated. It is believed that this is a far more sensitive approach to measuring small intestinal damage.

Figures 8A, 8B:
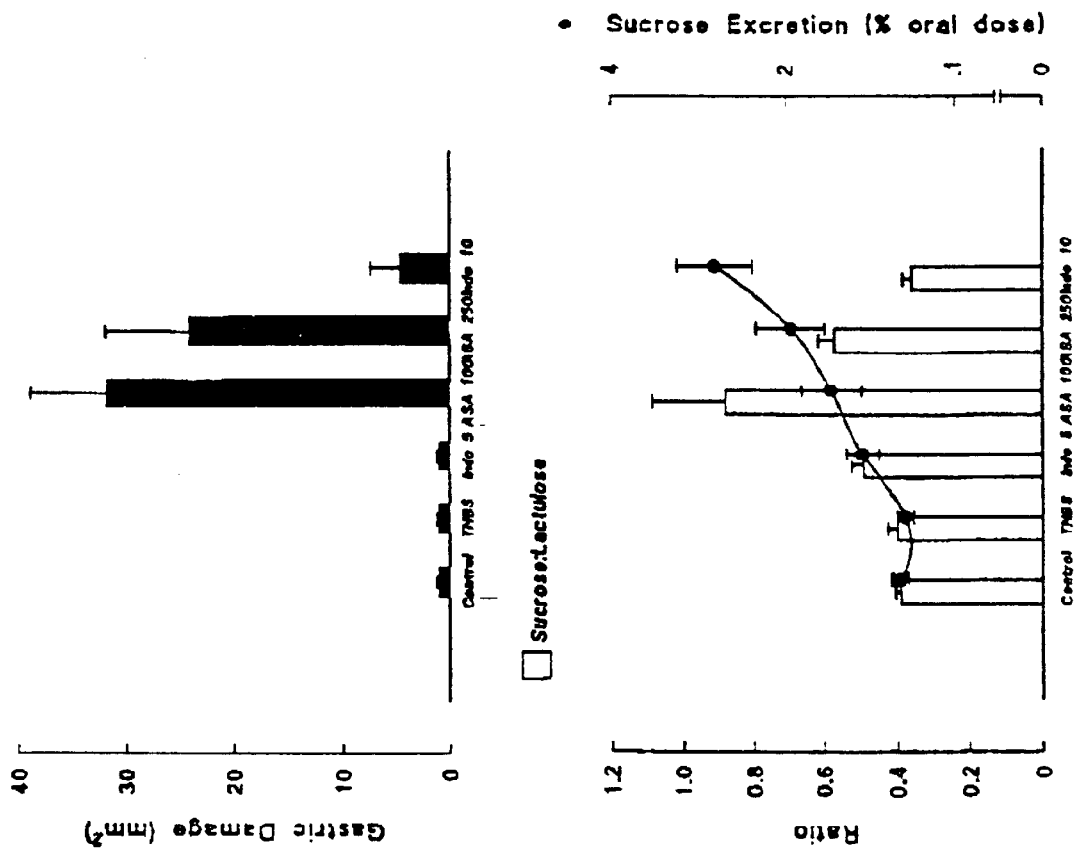
FIG. 8(*a*) is a graph illustrating gastric damage compared to the dosing agent.
Figure 8A:
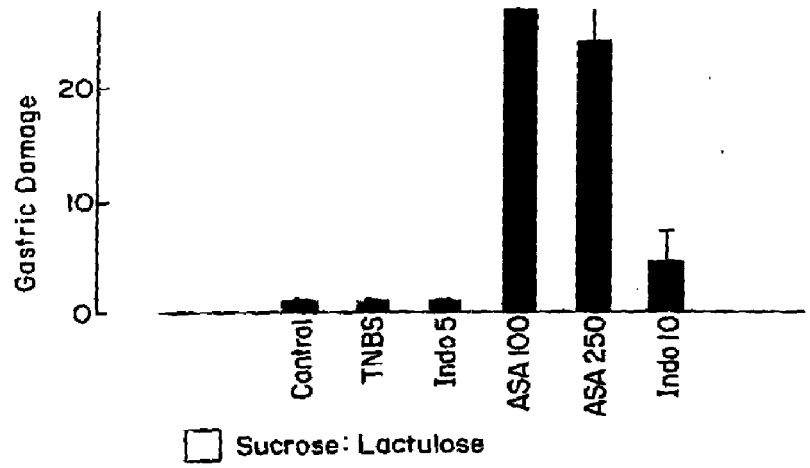
Figure 8B:
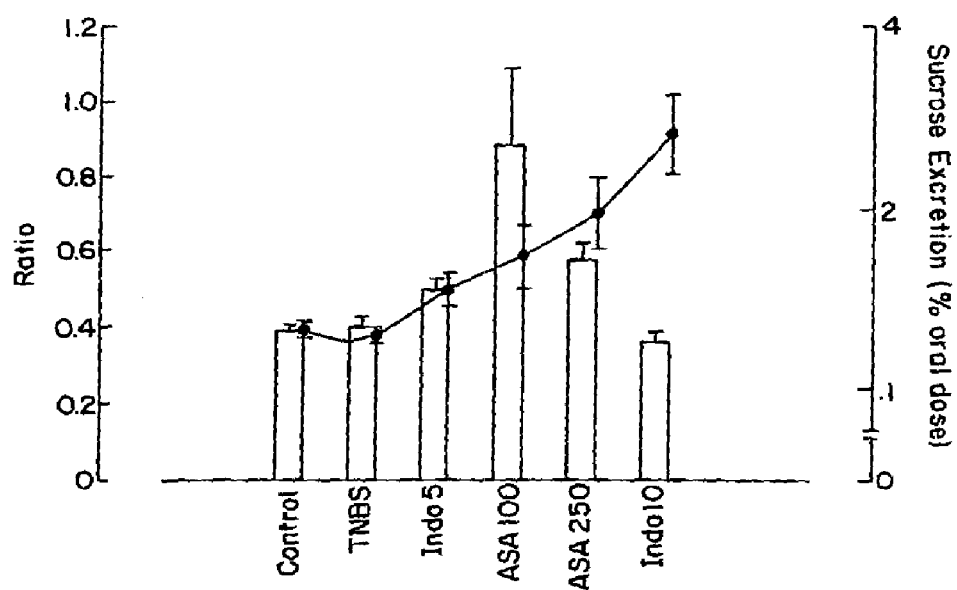

In FIG. 8(a) gastric damage elicited by the various drugs is illustrated. Quite clearly neither control animals nor those treated with TNBS had any evidence of damage. The greatest degree of gastric damage was seen in those animals receiving aspirin. High dose indomethacin produced a significant degree of gastric damage but clearly not as severe as that seen in aspirin treated animals. Looking at FIG. 8(b), it is clear that if only sucrose excretion is examined, shown as the filled circles, this pattern is not observed. In contrast to the visual damage score high dose indomethacin caused the greatest increase in sucrose excretion. On one hand sucrose has been demonstrated to reliably increase with increasing gastric damage.

However in this experiment sucrose permeability is greatest in animals with less gastric damage.

It is possible that one explanation for this discrepancy is the difference in type of damage produced by these drugs. Aspirin produces damage that is more readily apparent to the eye than indomethacin. However, it is also possible that a significant proportion of the increased sucrose permeability seen with high dose indomethacin was not due to gastric damage but rather small intestinal damage.

Considering this possibility it is interesting to examine the ratios shown in FIG. 8(b). The first is the sucrose/lactulose ratio. This ratio can be interpreted as whether damage occurs proximally or distally. If damage occurred both in the stomach and small intestine to an equivalent degree then both the sucrose excretion and the lactulose/mannitol ratio would be elevated. However, the sucrose/lactulose ratio should remain constant. Using this interpretation it is apparent that aspirin produces a significant increase in this ratio. Therefore, it is believed that aspirin produces more proximal damage which is consistent with the visual damage score. High dose indomethacin does not elevate this ratio suggesting that gastric and small intestinal damage has occurred to an equivalent extent. This normal ratio cannot be meaningfully interpreted in the absence of both the sucrose permeability and the lactulose/mannitol ratio. These measurements prove that damage has occurred to both the stomach and small intestine while the normal sucrose/lactulose ratio suggests that there is no proximal specificity to this damage.

The above-described data show that site specific gastrointestinal damage can be determined using a combination of disaccharides. Sucrose is relatively specific for the stomach but also increases with diffuse small intestinal damage. The lactulose/mannitol ratio is a reasonable test of small intestinal damage but cannot measure colonic damage. Sucralose is an interesting disaccharide that appears to be insensitive to gastric damage. It is believed that this is probably a reflection of the small surface area of the stomach. With diffuse small intestinal damage sucralose permeability increases and it is also significantly increased in animals with isolated colonic damage. Therefore, sucralose can be used to quantify colonic damage provided it is used in combination with other disaccharides to exclude small intestinal damage.

Other variations and modifications of this invention will be obvious to those skilled in this art. This invention is not to be limited except as set forth in the following claims.

I claim:

1. A composition for site specific detection of mucosal lesions of the stomach, small intestine or colon comprising:
   (a) a first disaccharide that does not degrade in the colon, small intestine or stomach, said first disaccharide present in an amount of about 1 to about 3 percent by dry weight of the composition;
   (b) a second disaccharide that degrades in the colon but does not degrade in the small intestine or stomach, said second disaccharide present in an amount of about 4 to about 10 percent by dry weight of the composition; and
   (c) a third disaccharide that degrades to its monosaccharides in the small intestine and not in the stomach, said third disaccharide present in an amount of about 87 to about 97 percent by dry weight of the composition.

2. A composition according to claim 1 wherein (a) said first disaccharide is sucralose, (b) said second disaccharide is lactulose and (c) said third disaccharide is sucrose.

3. A composition according to claim 2, further comprising mannitol.

4. A composition according to claim 1, further comprising an aqueous carrier.

5. A composition for assaying mucosal lesions of the stomach, small intestine or colon comprising: (a) sucralose, (b) lactulose, and (c) sucrose, each of (a), (b) and (c) present in an amount effective for detection in an assay of the urine of a patient suffering from mucosal lesions of the stomach, small intestine-or colon after administration of said composition thereto.

6. A composition according to claim 5, further comprising mannitol.

7. A composition according to claim 6, further comprising an aqueous carrier.

8. A composition for the detection of mucosal lesions of the small intestine or colon comprising:

(a) a first disaccharide that does not degrade in the colon, small intestine or stomach; and (b) a second disaccharide that degrades in the colon but does not degrade in the small intestine or stomach, wherein said first disaccharide is sucralose present in an amount of about 10 to about 75 percent by dry weight of the disaccharides and said second disaccharide is lactulose present in an amount of about 25 to about 90 percent by dry weight of the disaccharides.

9. A method for site-specific detection of mucosal lesions of the stomach, small intestine or colon in a patient comprising the steps of:

(a) administering to the patient concurrently or sequentially the following disaccharides (i) a first disaccharide that does not degrade in the colon, small intestine or stomach;

(ii) a second disaccharide that degrades in the colon but does not degrade in the small intestine or stomach; and (iii) a third disaccharide that degrades to its monosaccharides in the small intestine and not in the stomach; and (b) assaying the patient's urine for the presence of the disaccharides administered in step (a) to determine the existence or extent of mucosal lesions in the stomach, small intestine or the colon.

10. The method according to claim 9, wherein said first disaccharide is sucralose, said second disaccharide is lactulose and said third disaccharide is sucrose.

11. The method according to claim 10, further comprising administering mannitol with said disaccharides of step (a) and assaying for said mannitol.

12. A method for detecting mucosal lesions in the small intestine or colon comprising the steps of:

(a) administering to the patient concurrently or sequentially the following disaccharides (i) a first disaccharide that does not degrade in the colon, small intestine or stomach; and (ii) a second disaccharide that degrades in the colon but does not degrade in the small intestine or stomach; and (b) assaying the patient's urine for the presence of the disaccharides administered in step (a) to determine the existence or extent of mucosal lesions in the small intestine or the colon.

13. A method according to claim 12 wherein said first disaccharide is sucralose and said second disaccharide is lactulose.

* * * * *

UNITED STATES PATENT AND TRADEMARK OFFICE
CERTIFICATE OF CORRECTION

PATENT NO.    : 6,037,330
DATED         : March 14, 2000
INVENTOR(S)   : Jonathan B. Meddings It is certified that error appears in the above-identified patent and that said Letters Patent is hereby corrected as shown below:

Title page,
Item [56], References Cited, FOREIGN PATENT DOCUMENTS, insert:
-- 2,131,218    1995    CANADA --;
OTHER PUBLICATIONS, after "Cobden, L., et al.,", "*Gut,*" should read -- *Gut, 21*, --.

Drawings,
Sheets 1 through 8 are printed upside down;
Figures 8A and 8B, Figure headings have been relabeled for legibility.

Column 1,
Line 10, "relate" should read -- relates --;
Line 53, "disclose" should read -- discloses --.

Column 2,
Line 19, "ing (a)" should read -- ing: (a) --;
Line 53, "percent" should read -- percentage --;
Line 60, "TNBS)." should read -- (TNBS); --.

Column 4,
Line 23, "degardes" should read -- degrades --;
Line 32, "disaccharide" should read -- disaccharides --.

Column 5,
Line 61, "mg." should read -- mg --.

Column 6,
Line 22, "EtOH" should read -- ETOH --;
Line 49, "over night" should read -- overnight --.

UNITED STATES PATENT AND TRADEMARK OFFICE
CERTIFICATE OF CORRECTION

PATENT NO. : 6,037,330
DATED : March 14, 2000
INVENTOR(S) : Jonathan B. Meddings It is certified that error appears in the above-identified patent and that said Letters Patent is hereby corrected as shown below:

Column 11,
Line 2, "intestine-or" should read -- intestine or --.

Signed and Sealed this

Seventeenth Day of May, 2005

JON W. DUDAS
*Director of the United States Patent and Trademark Office*